United States Patent
Mitchell, Jr. et al.

(10) Patent No.: US 6,893,631 B1
(45) Date of Patent: May 17, 2005

(54) SHAVING SOAP AND AFTERSHAVE GEL AND METHODS OF USE THEREOF

(75) Inventors: Clarence Mitchell, Jr., Nashville, TN (US); Willard Sanders, Old Hickory, TN (US)

(73) Assignee: Mitchell & Sons, LLC, Nashville, TN (US)

( * ) Notice: Subject to any disclaimer, the term of this patent is extended or adjusted under 35 U.S.C. 154(b) by 306 days.

(21) Appl. No.: 10/171,150

(22) Filed: Jun. 13, 2002

Related U.S. Application Data

(60) Provisional application No. 60/298,222, filed on Jun. 14, 2001.

(51) Int. Cl.[7] ............................. A61K 7/06; A61K 7/15
(52) U.S. Cl. ......................................... 424/73; 424/401
(58) Field of Search ................................... 424/73, 401

(56) References Cited

U.S. PATENT DOCUMENTS

| | | | |
|---|---|---|---|
| 4,273,684 A | 6/1981 | Nagashima et al. | 252/544 |
| 4,528,111 A | 7/1985 | Su | 252/107 |
| 5,034,220 A | 7/1991 | Helioff et al. | 424/73 |
| 5,271,942 A | 12/1993 | Heverhagen | 424/451 |
| 5,308,643 A | 5/1994 | Osipow et al. | 424/73 |
| 5,403,864 A | 4/1995 | Bruch et al. | 514/721 |
| 5,431,906 A | 7/1995 | Mohseni et al. | 424/73 |
| 5,480,633 A | 1/1996 | Simion et al. | 424/70.1 |
| 5,523,017 A | 6/1996 | Moran et al. | 252/174.21 |
| 5,529,712 A | 6/1996 | Sano et al. | 252/108 |
| 5,560,859 A | 10/1996 | Hartmann et al. | 510/135 |
| 5,665,340 A | 9/1997 | Stoner et al. | 424/73 |
| 5,730,965 A | 3/1998 | Rapaport | 424/70.1 |
| 5,786,311 A * | 7/1998 | Zyngier et al. | 510/147 |
| 5,837,661 A | 11/1998 | Evans et al. | 510/122 |
| 5,853,710 A | 12/1998 | Dehan et al. | 424/73 |
| 5,888,490 A | 3/1999 | Hall-Puzio | 424/73 |
| 5,902,574 A | 5/1999 | Stoner et al. | 424/73 |
| 5,929,019 A | 7/1999 | Puvvada et al. | 510/406 |
| 5,956,848 A | 9/1999 | Tseng et al. | 30/41 |
| 5,976,520 A | 11/1999 | Babinski et al. | 424/73 |
| 6,008,246 A | 12/1999 | Ito et al. | 514/458 |
| 6,012,463 A | 1/2000 | Mitchell, Jr. | 132/200 |
| 6,014,975 A | 1/2000 | Benzinger | 132/200 |
| 6,046,238 A | 4/2000 | Yu et al. | 514/553 |
| 6,096,702 A | 8/2000 | Ramirez et al. | 510/421 |
| 6,207,694 B1 | 3/2001 | Murad | 514/396 |
| 6,265,370 B1 * | 7/2001 | Newbegin | 510/458 |

* cited by examiner

*Primary Examiner*—James M. Spear
(74) *Attorney, Agent, or Firm*—Waddey & Patterson, P.C.; Lucian Wayne Beavers

(57) ABSTRACT

This invention relates to compositions of a shaving soap and an aftershave gel that are used to prevent or reduce the occurrence of folliculitis. The shaving soap and aftershave gel compositions disclosed herein are formulated to specifically remedy the problem of folliculitis. Disclosed herein is also a method of using the shaving soap and aftershave gel in order to prevent folliculitis.

20 Claims, No Drawings

SHAVING SOAP AND AFTERSHAVE GEL AND METHODS OF USE THEREOF

This application claims benefit of U.S. patent application Ser. No. 60/298,222 filed Jun. 14, 2001, entitled "Shaving Soap Formula and Method" which is hereby incorporated by reference.

Be it known that we, Clarence Mitchell Jr., a citizen of The United States, residing at 3608 Fairmeade Drive, Nashville, Tenn. 37218; Willard Sanders, a citizen of The United States, residing at 344 Lake Shore Drive, Old Hickory, Tenn. 37138; have invented a new and useful "Shaving Soap and Aftershave Gel and Methods of Use Thereof."

FIELD OF THE INVENTION

The present invention relates to a shaving soap formulation, aftershave gel and shaving method to reduce the occurrence of folliculitis.

BACKGROUND OF THE INVENTION

Many people with sensitive skin, particularly the African American community, have suffered from folliculitis. Folliculitis is the inflammation of one or more follicles, especially of the hair. The general cause of folliculitis is ingrown hair or hair bumps. The ingrown hair and microbes associated with the ingrown hair cause the sometimes extreme skin irritation associated with folliculitis.

Different types of shaving agents and gels have been provided. For example, U.S. Pat. No. 5,034,220 discloses a non-aerosol shaving gel which consists essentially of a polyvinylmethylether-maleic anhydride (PVM/MA) copolymer, a water-soluble salt of a higher fatty acid $C_{10}$–$C_{24}$ water soluble soap, and water. U.S. Pat. No. 5,271,942 discloses an agent for reducing the growth of human hair, which contains plant extracts such as hamamelis, Aloe Vera gel. U.S. Pat. No. 5,308,643 provides a shaving preparation comprising an aqueous soap solution, a volatile organic liquid and a non-volatile, water insoluble organic liquid. U.S. Pat. No. 5,431,906 discloses a solid shaving composition which comprises a soap base, humectant such as glycerin, a high molecular weight polyethylene oxide, at least one antioxidant such as tocopherol, at least one anticorrosion agent such as a quaternary ammonium salt, and at least one emulsifying agent such as glyceryl stearate.

Other shaving systems or methods have also been provided. Examples 15 include U.S. Pat. No. 5,665,340, which discloses a shaving system. Also, U.S. Pat. No. 6,014,975, which discloses a method of shaving, which includes the step of providing a bath comprising witch hazel, lubricant, etc. U.S. Pat. No. 5,730,965, discloses a method to treat and/or prevent seborrheic dermatitis of the scalp and other hair bearing areas, dandruff or psoriasis by topically applying to the skin and washing the skin in a shampoo containing an effective amount of a treatment composition containing chloroxylenol. U.S. Pat. No. 5,403,864 describes a rapidly-acting topical alcohol base anti-microbial composition using Tricolsan and Chloroxylenol. U.S. Pat. No. 5,956,848 discloses a wet shaving system with a polymeric shaving aid composite mounted to the razor as adjacent exposed lengthwise-extending portions.

A shaving method for reducing folliculitis which delineates precise razor pulling techniques and methods of preparing a skin surface to be shaved is disclosed in U.S. Pat. No. 6,012,463 to Mitchell, Jr.

SUMMARY OF THE INVENTION

What is needed is a shaving soap and aftershave gel that may be used to reduce the occurrence of folliculitis. The present invention discloses shaving soap compositions and aftershave gel compositions that provide surprising results when used to reduce the occurrence of folliculitis. Also disclosed herein are methods of treating folliculitis and methods of reducing the occurrence of folliculitis.

Accordingly, one aspect of the present invention is a shaving soap that comprises about 800–1200 parts by weight of a base soap; about 10–70 parts by weight of a surfactant package, wherein the surfactant package provides copious foaming to the shaving soap; and about 2–40 parts by weight of mango butter.

Another aspect of the present invention is that in certain embodiments the base soap includes about 5% to about 30% by weight of distilled water; about 2% to about 50% by weight of palm oil; about 2% to about 30% by weight of coconut oil; about 2% to about 40% by weight of castor oil; and about 4% to about 20% by weight of sodium hydroxide. Also, the base soap may further comprise about 2% to about 50% by weight of special denatured alcohol 40; about 2% to about 30% by weight of glycerin; and about 2% to about 40% by weight of sorbitol.

Still another aspect of the invention is that the surfactant package further comprises about 30% to about 85% by weight of ammonium laureth sulfate; about 2% to about 60% by weight of ammonium $C_{14-16}$ olefin sulfonate; about 1% to about 25% by weight of lauramide DEA; about 0.1% to about 0.7% by weight of tetrasodium EDTA; and about 0.05% to about 1.0% by weight of 2-hydroxyl-1,2,3 propanetricarboxylic acid. In certain embodiments, the surfactant package has a pH from about 5.5 to about 7.

Another aspect of the present invention is that the shaving soap may also include about 2 to about 15 parts by weight of triclosan; about 5 to about 20 parts by weight of lysine carboxymethylcysteninate; and about 5 to about 20 parts by weight of lysine thiazolidinecarboxylate. The shaving soap may also include about 2 to about 40 parts by weight of nonoxynol-10 carboxylic acid; about 2 to about 40 parts by weight of octyl dodecyl benzoate; about 1 to about 5 parts by weight of vitamin E; and about 1 to about 10 parts by weight of aloe vera.

Another aspect of the present invention is an aftershave gel, comprising about 0.5% to about 1.5% by volume of a base aftershave gel; about 0.5% to about 3% by volume of hamamelis; about 1% to about 30% by volume of a first mixture comprising about 0.5 grams to about 10 grams of camellia sinensis and about 8 ounces of distilled water; and about 1% by volume of dimethyol dimethyl (DMDM) hydantoin. The aftershave gel may also contain about 0.2% to about 1.5% by volume of aloe vera; about 0.2% to about 1.5% by volume of a mixture of glyceryl polymethacrylate, propylene glycol and PVM/MA copolymer; or about 0.1% to about 3% by volume of propylene glycol.

Still another aspect of the present invention is a method of reducing folliculitis, comprising the steps of preparing a skin surface to be shaved, wherein preparing further comprises scrubbing the skin surface with a shaving soap comprising about 800–1200 parts by weight of a base soap; about 10–70 parts by weight of a surfactant package, wherein the surfactant package provides copious foaming to the shaving soap; and about 2–40 parts by weight of mango butter; shaving the skin surface; and applying an aftershave gel to the skin surface, wherein the aftershave gel further comprises about 0.5% to about 1.5% by volume of a base aftershave gel; about 0.5% to about 3% by volume of hamamelis; about 1% to about 30% by volume of a first mixture comprising about 0.5 grams to about 10 grams of *camellia sinensis* and about 8 ounces of distilled water; and about 0.05% to about 1% by volume of DMDM hydantoin.

Another aspect of the present invention of reducing folliculitis is using a soap that further comprises about 5% to about 30% by weight of distilled water; about 2% to about 50% by weight of palm oil; about 2% to about 30% by weight of coconut oil; about 2% to about 40% by weight of castor oil; and about 4% to about 20% by weight of sodium hydroxide.

Still another aspect of the pre sent invention of reducing folliculitis is preparing the skin surface by saturating a boar's hair brush with warm water, inserting the boar's hair brush into a cup containing the shaving soap, and mixing until a lather develops. After the lather develops, the lather is applied to the skin surface with the boar's hair brush using a circular motion.

Another aspect of the present invention is applying the aftershave gel to the skin surface by providing a dime-sized amount of the aftershave gel on a first hand; rubbing the first hand against a second hand so that the aftershave gel is distributed on the first hand and the second hand; and distributing the aftershave gel from the first hand to the skin surface with a single downward motion of the first hand, wherein the single downward motion starts at a cheek bone, moves toward a chin, and finishes at a bottom of a neck, so that the skin surface that has been shaved receives the aftershave gel. Also, the aftershave gel from the second hand may be distributed to the skin surface with a single downward motion of the second hand, wherein the single downward motion starts at the cheek bone, moves toward the chin, and finishes at the bottom of the neck, so that the skin surface that has been shaved receives the aftershave gel. The aftershave gel may also contain about 0.2% to about 1.5% by volume of aloe vera; about 0.2% to about 1.5% by volume of a mixture of glyceryl polymethacrylate, propylene glycol and PVM/MA copolymer; and about 0.1% to about 3% by volume of propylene glycol.

DESCRIPTION OF THE INVENTION

The present invention relates compositions for and methods of reducing folliculitis. More specifically, the present invention further relates to a shaving soap, shaving cream, or shaving lotion that helps prevent the occurrence of folliculitis and reduce the occurrence of folliculitis. The present invention further relates to a shaving gel (i.e. an aftershave gel) that cooperates with the shaving lotion and method of the present invention in preventing and reducing the occurrence of folliculitis. The aftershave gel also keeps the skin from drying and prevents the ashen color associated with dry dark skin.

The method of the present invention comprises preparing a skin surface to be shaved with non-oil-based cleanser; shaving the skin surface including shaving only a plurality of hairs above a skin line located at the skin surface; and pulling a razor in a plurality of consistent unidirectional motions to carry out the step of shaving. This method is described in detail in U.S. Pat. No. 6,012,463 to Mitchell, Jr.

The present invention additionally discloses methods of using the compositions disclosed herein in order to prevent or reduce the occurrence of folliculitis. Accordingly, the shaving soap formula and aftershave gel of the present invention can be used in connection with the above-described method.

As used herein, "% by weight" is defined as generally understood in the art. For example, % by weight means the percentage of the whole as measured by weight. Thus, if a mixture has a total weight of 100 grams and contains 10 g of palm oil, then the mixture has 10% by weight of palm oil.

As used herein, "% by volume" is defined as generally understood in the art. Since % by volume means the percentage of the whole as measured by volume, if, for example, a mixture has a total volume of 100 milliliters and contains 10 milliliters of propylene glycol, then the mixture has 10% by volume of propylene glycol.

As used herein, "parts by weight" means that components parts are added as units of measurement having identical weight. Thus, parts by weight does not require the addition of components as % by weight or % by volume. For example, the following formula would be prepared as follows:

| Ingredients | Parts by weight |
| --- | --- |
| Formula 1 | 1000 |
| Formula 2 | 30 |
| Mango Butter | 10 |
| Nonoxynol-10 Carboxylic Acid | 10 |

If the predetermined unit of measurement is one gram, then the above-mentioned final composition is prepared by adding 1000 g of the Formula 1 composition, 30 g of the Formula 2 composition, 10 g of Mango Butter, and 10 g Nonoxynol-10 Carboxylic Acid.

Base Soap

The shaving soap composition for the present invention comprises a base soap formula. Preferably, the base soap formula provides a good lather and provides a good feel or a smooth feel to facilitate a good shave. In that regard, one of ordinary skill in the art could selection and choose a suitable base soap formulation for the present invention.

Preferably, the base soap formula of the present invention comprises sodium hydroxide (commercially available from Spectrum, 14422 South San Pedro St. Garden, Calif. 90248) and agents that are saponified with sodium hydroxide. In one embodiment, the oils disclosed herein are saponified with sodium hydroxide. Preferably, the oils include palm oil (commercially available from Jarchem, 414 Wilson Avenue, Newark, N.J. 07105), coconut oil (commercially available from Jarchem, 414 Wilson Avenue, Newark, N.J. 07105), and/or castor oil (commercially available from Arista Ind., 557 Danbury Rd., Wilton, Conn. 06897). Preferably, the soap further comprises at least one of: alcohol for clarity, glycerin (commercially available from Dow Chemical, P.O. Box 1206, Midland, Md. 48642) (from vegetable oil) for lubricity, and sorbitol to assist in a smooth feel and to help the soap set up. Preferably the alcohol is special denatured alcohol 40 (SDA 40).

More preferably, the base soap formula of the present invention is Formula 1, below:

| Ingredient | % by weight |
| --- | --- |
| Palm Oil | 2–50 |
| Coconut Oil | 2–30 |
| Castor Oil | 2–40 |
| Sodium Hydroxide | 4–20 |
| Distilled Water | 5–30 |

-continued

| Ingredient | % by weight |
| --- | --- |
| SDA 40 (alcohol) | 2–50 |
| Glycerin | 2–30 |
| Sorbitol | 2–40 |

Surfactant Package

Preferably, the soap formula of the present invention includes a surfactant package. The surfactant package should give copious foaming to the soap formulation. Preferably, the surfactant package yields an abundance of small bubbles. Preferably, the surfactant package comprises primary and secondary surfactants that promote small bubbles and copious foaming.

Therefore, the ingredients to the surfactant package may be changed or modified as long as the desired results are achieved. That is, variations in the formula may change the quality of the foam and how long the foam lasts.

Preferably, the biodegradable surfactant package of the present invention includes the ingredients of Formula 2, below:

| Ingredient | % by weight |
| --- | --- |
| Ammonium Laureth Sulfate | 30–85 |
| Ammonium $C_{14-16}$ Olefin Sulfonate | 2–60 |
| Lauramide DEA | 1–25 |
| Tetrasodium EDTA | 0.1–0.7 |
| 2-Hydroxyl-1,2,3 Propanetricarboxylic Acid | 0.05–1.0 |

The surfactant package is prepared by mixing the above-mentioned components at ambient temperatures. In certain embodiments, the components are mixed at from about 70 degrees Fahrenheit (F) to about 85 degrees F. In other embodiments, the components are mixed at from about 85 degrees F. to about 130 degrees F. The components described in Formula 2 are mild primary and secondary surfactants that promote small bubbles and copious foaming. In other embodiments, sodium laureth sulfate is used in place of the ammonium laureth sulfate.

Tetrasodium EDTA (commercially available from Pilot Chemical, 11756 Burke St., Santa Fe Springs, Calif. 90670) acts as a chelating agent to improve long term UV stability, and 2-hydroxyl-1,2,3-propanetricarboxyic acid (commercially available from Pilot Chemical, 11756 Burke St., Santa Fe Springs, Calif. 90670), an organic acidulant, adjusts the pH and helps stabilize the surfactant package. Preferably, the pH of the surfactant package is approximately 5.5–7.

Active Ingredients

In certain embodiments, the shaving soap formulation of the present invention comprises the base soap formula, surfactant package and active ingredients.

In one embodiment, the shaving soap formulation of the present invention includes the base soap formula, surfactant package, and triclosan (commercially available from McIntyre Group, 24601 Govenors Hwy, Univ Pk, Ill. 60466). Preferably, the shaving soap formulation of the present invention comprises the base soap formula, a surfactant package, triclosan, lysine carboxymethylcysteinate and lysin thiazolidinecarboxylate (commercially available from Sinerga Via Pitagora 11 Milano Italy). The ingredients are sulfur based treatments, i.e. water-soluable anti-seborrheic in nature, which treat excessive sebaceous secreations. The active mechanism is that the sebostatic function, which is typical of organic sulfur when it binds with an amino acid, is achieved by normalizing the spread of sebum on skin and hair. It inhibits the activity of the enzyme which amplifies the androgen signal responsible for hyper-seborrhea, constricts dilated pores, and limits bacterial proliferation which can contribute to acne.

In other embodiments, the shaving soap formulation may include additional products such as Nonoxynol-10 Carboxylic Acid (commercially available from Fintex, P.O. Box 164, Spencer, N.C. 28159) and Octyl Dodecyl Benzoate (commercially available from Fintex, P.O. Box 164, Spencer, N.C. 28159) which provide additional glide for the razor and help prevent razor burn. These two ingredients are also beneficial to prevent the greying of skin due to frequent shaving. Additional agents for smoothness may also be added which gives additional glide to the razor and provide a nice feel after the soap is rinsed away. In a preferred embodiment of the present invention, mango butter (commercially available from Trivent Chemical Co., 4266 U.S. Route 1, Monmouth, N.J. 08852) may be added as the smoothness agent. A stabilizer may also be added. In a preferred embodiment of the present invention, vitamin E (commercially available from Spectrum, 14422 South San Pedro St,. Garden, Calif. 90248) may be added as a stabilizer. Additionally, vitamin E is believed to be good for the skin. Aloe Vera (commercially available from Terry Labs, 390 Wickham Road, Melborn, Fla. 32935-8647) may be added to provide a smoothness to the skin and to help with razor burn. Additionally, color and fragrance may be added to achieve desired characteristics of the shaving soap formulation.

The Shaving Soap

A preferred shaving soap formulation of the present invention is Formula 3, below:

| Ingredients | Parts by weight |
| --- | --- |
| Formula 1 | 800–1200 |
| Formula 2 | 10–70 |
| Mango Butter | 2–40 |
| Nonoxynol-10 Carboxylic Acid | 2–40 |
| Octyl Dodecyl Benzoate | 2–40 |
| Vitamin E | 1–5 |
| Triclosan | 2–15 |
| Aloe Vera | 1–10 |
| Lysine Carboxymethylcysteninate and Lysine Thiazolidinecarboxylate | 5–20 |
| Color and Fragrance | q.s. |

Another embodiment of the shaving soap formula of the present invention may include benzoyl peroxide. Preferably, benzoyl peroxide is present in the amount of approximately 2.5% by weight, although this amount may change to achieve the particular desired results.

An Aftershave Gel

The aftershave gel of the present invention includes a base aftershave gel formula. The function of the base aftershave gel is to provide the base gel to which other components are added. The base aftershave gel may be varied as described herein by one of ordinary skill in the art to achieve a particular result.

Preferably, the base aftershave gel of the present invention is prepared from two intermediate components. The first intermediate, also called a first mixture, is prepared according to Formula 4. The second intermediate used in the preparation of the base aftershave gel is prepared according to Formula 5:

Formula 4

*Camellia Sinensis* 0.5–10 grams (also known as Japanese Green Tea, commercially available from Draco, 1701 Fortune Dr., San Jose, Calif. 95131)

Distilled Water 8 ozs.

| Formula 5 | |
|---|---|
| Polyacrylic Acid Polymer | 5–10 grams |
| Distilled Water | 1 gallon |
| Triethanolamine (TEA) | 0.05–2.0% by weight to reach preferred viscosity of 5,000–20,000 centipoises (cps) as measured by a Brookfield RV viscometer. |

The shaving gel of the present invention is formed by adding the base aftershave gel formula with the below-listed active ingredients.

Hamamelis is witch hazel (commercially available from Dragoco Inc., 10 Gordon Drive, Totowa, N.J. 09512). In certain embodiments, it is added to provide lubricity. In certain embodiments, Aloe Vera is. Additionally, a mixture of glyceryl polymethacrylate and propylene glycol and PVM/MA copolymer, also known under the trademark of Lubriderm® (commercially available from ISP Van Dyk, Main and Williams St., Belleville, N.J. 07109) may be added to help leave the shaver with a nice feel. In other embodiments, propylene glycol (commercially available from Spectrum, 14422 S. San Pedro St., Garden, Calif. 90248) may also be added to leave the shaver with a nice feel. Dimethyol dimethyl (DMDM) hydantoin (commercially available from McIntyre Group, 24601 Governors Hwy., Univ Pk, Ill. 60466) is added as a preservative. Additionally, fragrance and color may be added. Additionally, alcohol FDA #40 may be added to promote drying. In still other embodiments, a combination of the above-mentioned components are added to the aftershave gel formulation.

A preferred embodiment of the aftershave gel formulation of the present invention is listed in Formula 6, below:

| Ingredient | % by volume |
|---|---|
| Base aftershave gel | 0.5–1.5 |
| Hamamelis | 0.5–3 |
| Aloe Vera | 0.2–1.5 |
| A mixture of Glyceryl Polymethacrylate, Propylene Glycol and PVM/MA copolymer | 0.2–1.5 |
| a first mixture, also called Formula 4 | 1–30 |
| Propylene Glycol | 0.1–3 |
| DMDM Hydantoin | 0.05–1.0 |
| Fragrance | q.s. |
| Color | q.s. |

Method of Preventing or reducing the Occurrence of Folliculitis

As stated above, the shaving soap and aftershave gel of the present invention may be used as part of the shaving method comprising the shaving techniques described in U.S. Pat. No. 6,012,463 issued on Jan. 11, 2000 to Mitchell, Jr., which is hereby incorporated by reference in its entirety.

An additional embodiment of the present invention comprises the above described shaving method including the additional steps of using the shaving soap disclosed herein and applying the aftershave gel which is also disclosed herein. In another embodiment, the method of reducing folliculitis comprises preparing a skin surface for shaving by applying the shaving soap; shaving the skin surface; and treating the skin surface by applying the aftershave gel.

In another embodiment, the method of applying the shaving soap comprises saturating a boar's hair brush with warm water, inserting the boar's hair brush into a cup containing the shaving soap, and mixing until a thick lather develops.

In certain embodiments, the method of applying the aftershave gel comprises providing a dime-sized amount, approximately three small drops, of the aftershave gel, rubbing hands together to evenly distribute the aftershave gel, applying the aftershave gel to the skin surface by beginning at the cheek bone and using a single downward motion toward the chin, applying the aftershave gel to the bottom of the chin and neck by beginning at the bottom of the chin and using a single downward motion move toward the neck with a first hand, making sure to cover the entire shaved neck area. In other embodiments, the applying steps are repeated. In still other embodiments, if the dime-sized amount of aftershave gel is not enough to cover the shaved areas, more aftershave gel is added.

All patents and publications referred to in this application are herein expressly incorporated by reference. Also, unless indicated otherwise within this document, the components described herein may be mixed at an ambient temperature.

EXAMPLES

Example 1

Preparation of the Base Soap

A base shaving soap is prepared according to the following steps and makes use of the components and amount of each component that are listed below. First, heat 21 grams of palm oil, 8 grams of coconut oil, and 13 grams of castor oil to 145 degrees Fahrenheit (F). Mix 6 grams of sodium hydroxide and 8 grams of distilled water, then heat to 135 degrees F. Slowly add the sodium hydroxide and distilled water to the palm oil, coconut oil, and castor oil. Let the mixture reach a medium trace. Remove heat source and leave the mixture in a hot water bath for 2 hours until it goes into a gel phase and saponifies. After 2 hours add 19 grams of SDA 40 (alcohol) and 5 grams of glycerin and heat to 150 degrees F. Then, add 12 grams of sorbitol and 8 grams of distilled water and cool down slowly to 140 degrees F. Controlled cooling below 140 degrees F. is not required.

| Ingredient | weight | % by weight |
|---|---|---|
| Palm Oil | 21 grams | 21 |
| Coconut Oil | 8 grams | 8 |
| Castor Oil | 13 grams | 13 |
| Sodium Hydroxide | 6 grams | 6 |
| Distilled Water | 16 grams | 16 |
| SDA 40 (alcohol) | 19 grams | 19 |
| Glycerin | 5 grams | 5 |
| Sorbitol | 12 grams | 12 |

Example 2

Preparation of a Surfactant Package

The following components are mixed at about 70 degrees F. Commercial sources for each component are listed within this application. Additional commercial sources include: Pilot Chemical, 11756 Burke St., Santa Fe Springs, Calif. 90670 for Ammonium Laureth Sulfate, and Ammonium $C_{14-16}$ Olefin Sulfonate.

| Ingredient | weight | % by weight |
| --- | --- | --- |
| Ammonium Laureth Sulfate | 65.17 grams | 65.17 |
| Ammonium $C_{14-16}$ Olefin Sulfonate | 32.02 grams | 32.02 |
| Lauramide DEA | 2.25 grams | 2.25 |
| Tetrasodium EDTA | 0.39 grams | 0.39 |
| 2-Hydroxyl-1,2,3 Propanetricarboxylic Acid | 0.17 grams | 0.17 |

Example 3

Preparation of the Shaving Soap

This example provides information regarding the preparation of the shaving soap. For this example, the weight assigned to each part to be added is one gram. Since each component is added as parts by weight, the amount of a given component is calculated by multiplying one gram by the value in the parts by weight column on the following table. Accordingly, 1000 grams of the base soap, also known as Formula 1, prepared in Example 1, is heated 190 degrees F. Then, 30 grams of the surfactant package, also known as Formula 2, prepared in Example 2, are added to the base soap. Next, 10 grams of mango butter, 10 grams of nonoxynol-10 carboxylic acid, 10 grams of octyl dodecyl benzoate, 2.5 grams of vitamin E, 5 grams of triclosan, 4 grams of aloe vera, and 10 grams of lysine carboxymethylcysteninate and lysine thiazolidinecarboxylate are added. If desired, add quantities of known components that are suitable for color. Cool the mixture containing the above-mentioned components to 175 degrees F. If desired, add quantities of known components that are suitable for fragrance. Pour the mixture into a mold and allow to cool.

| Ingredients | weight | parts by weight |
| --- | --- | --- |
| Formula 1 | 1000 grams | 1000 |
| Formula 2 | 30 grams | 30 |
| Mango Butter | 10 grams | 10 |
| Nonoxynol-10 Carboxylic Acid | 10 grams | 10 |
| Octyl Dodecyl Benzoate | 10 grams | 10 |
| Vitamin E | 2.5 grams | 2.5 |
| Triclosan | 5 grams | 5 |
| Aloe Vera | 4 grams | 4 |
| Lysine Carboxymethylcysteninate and Lysine Thiazolidinecarboxylate | 10 grams | 10 |
| Color and Fragrance | q.s. | q.s. |

Example 4

Preparation of a First Intermediate Component used in the Preparation of the Aftershave Gel Preparation of the first mixture, also called Formula 4, is accomplished as follows. Boil 8 oz of distilled water. Add 1.2 grams of *Camellia Sinensis*. Let steep for 1 hour.

| Camellia Sinensis | 1.2 grams |
| --- | --- |
| Distilled Water | 8 ozs. |

Example 5

Preparation of a Second Intermediate Component used in the Preparation of the Aftershave Gel Briefly, mix the polyacrylic acid polymer and distilled water. Continue to stir until the polyacrylic acid polymer is dissolved. Add small amounts of TEA and stir until a viscosity of 5,000–20,000 centipoises (cps) are reached using a Brookfield RV viscometer.

More specifically, 6 grams of the polyacrylic acid polymer (commercially available from BF Goodrich, 9911 Breksvill Rd., Cleveland, Ohio 44141) is dispersed in one gallon of distilled water. It is polymeric in nature and forms the gel. The TEA (commercially available from Dow Chemical, P.O. Box 1206, Midland, Md. 48642) is a pH adjuster to activate the polyacrylic acid polymer into a gel.

| Polyacrylic Acid Polymer | 6 grams |
| --- | --- |
| Distilled Water | 1 gallon |
| Triethanolamine (TEA) | add to thickness of 5,000–20,000 cps |

Example 6

Preparation of Aftershave Gel

This example provides information that allows the preparation of three liters of the aftershave gel. First, 60 ml of the first intermediate component, prepared in Example 4, is mixed with 2715 ml of the second intermediate component, prepared in Example 5. The mixture of these two intermediates results in the base aftershave gel. The two above-mentioned components must be mixed before any other ingredients are added.

All of the below-mentioned components, except for the first intermediate component and the second intermediate component, are mixed at about 70–90 degrees F. If desired, quantities of color and fragrance that are suitable are mixed with the base aftershave gel. After the first intermediate component is mixed with the second intermediate component, then the following components are added: 30 ml of hamamelis, 60 ml of aloe vera, 30 ml of a mixture of glyceryl polymethacrylate, propylene glycol and PVM/MA copolymer; 60 ml of Formula 4—as prepared in Example 4, 15 ml of propylene glycol, and 30 ml of DMDM hydantoin.

| Ingredients | volume | % by volume |
| --- | --- | --- |
| First intermediate component (Example 4) | 60 ml | 2 |
| Second intermediate component (Example 5) | 2715 ml | 90.5 |
| Hamamelis | 30 ml | 1 |
| Aloe Vera | 60 ml | 2 |
| A mixture of Glyceryl Polymethacrylate, Propylene Glycol and PVM/MA copolymer a first mixture, also called Formula 4 | 30 ml | 1 |
|  | 60 ml | 2 |
| Propylene Glycol | 15 ml | 0.5 |
| DMDM Hydantoin | 30 ml | 1 |
| Fragrance | q.s. | q.s. |
| Color | q.s. | q.s. |

All patents and publications disclosed above are expressly incorporated herein by reference in their entirety.

This invention thus being described, it will be obvious that the same may be varied in many ways. Such variations are not to be regarded as a departure from the spirit and scope of the present invention, and all such modifications as would be obvious to one of ordinary skill in the art are intended to be included within the scope of the following claims.

Thus, although there have been described particular embodiments of the present invention of a new and useful shaving soap and aftershave gel and methods of use thereof, it is not intended that such references be construed as limitations upon the scope of this invention except as set forth in the following claims.

What is claimed is:

1. A shaving soap, comprising:
   about 800 to about 1200 parts by weight of a base soap;
   about 10 to about 70 parts by weight of a surfactant package, wherein the surfactant package provides copious foaming to the shaving soap; and
   about 2 to about 40 parts by weight of mango butter;
   wherein the base soap further comprises
      about 5% to about 30% by weight of distilled water;
      about 2% to about 50% by weight of palm oil;
      about 2% to about 30% by weight of coconut oil;
      about 2% to about 40% by weight of castor oil; and
      about 4% to about 20% by weight of sodium hydroxide.

2. The shaving soap of claim 1, wherein the base soap further comprises:
   about 2% to about 50% by weight of special denatured alcohol 40;
   about 2% to about 30% by weight of glycerin; and
   about 2% to about 40% by weight of sorbitol.

3. The shaving soap of claim 1, wherein the surfactant package further comprises:
   about 2% to about 60% by weight of ammonium $C_{14-16}$ olefin sulfonate;
   about 1% to about 25% by weight of lauramide DEA;
   about 0.1% to about 0.7% by weight of tetrasodium EDTA; and
   about 0.05% to about 1.0% by weight of 2-hydroxyl-1,2,3 propanetricarboxylic acid.

4. The shaving soap of claim 3, wherein the surfactant package further comprises about 30% to about 85% by weight of ammonium laureth sulfate.

5. The shaving soap of claim 4, further comprising about 2.5% by weight of benzoyl peroxide.

6. The shaving soap of claim 3, wherein the surfactant package has a pH from about 5.5 to about 7.

7. The shaving soap of claim 3, further comprising:
   about 2 to about 15 parts by weight of triclosan;
   about 5 to about 20 parts by weight of lysine carboxymethylcysteninate; and
   about 5 to about 20 parts by weight of lysine thiazolidinecarboxylate.

8. The shaving soap of claim 7, further comprising:
   about 2 to about 40 parts by weight of nonoxynol-10 carboxylic acid;
   about 2 to about 40 parts by weight of octyl dodecyl benzoate;
   about 1 to about 5 parts by weight of vitamin E; and
   about 1 to about 10 parts by weight of aloe vera.

9. An aftershave gel, comprising:
   about 0.5% to about 1.5% by volume of a base aftershave gel;
   about 0.5% to about 3% by volume of hamamelis;
   about 1% to about 30% by volume of a first mixture comprising about 0.5 grams to about 10 grams of *camellia sinensis* and about 8 ounces of distilled water; and
   about 0.05% to about 1% by volume of DMDM hydantoin.

10. The aftershave gel of claim 9, further comprising: about 0.2% to about 1.5% by volume of aloe vera.

11. The aftershave gel of claim 9, further comprising: about 0.2% to about 1.5% by volume of a mixture of glyceryl polymethacrylate, propylene glycol and PVM/MA copolymer.

12. The aftershave gel of claim 9 further comprising: about 0.1% to about 3% by volume of propylene glycol.

13. The aftershave gel of claim 9, further comprising:
    about 0.2% to about 1.5% by volume of aloe vera;
    about 0.2% to about 1.5% by volume of a mixture of glyceryl polymethacrylate, propylene glycol and PVM/MA copolymer; and
    about 0.1% to about 3% by volume of propylene glycol.

14. A method of reducing folliculitis, comprising the steps of:
    preparing a skin surface to be shaved, wherein preparing further comprises scrubbing the skin surface with a shaving soap comprising about 800 to about 1200 parts by weight of a base soap; about 10 to about 70 parts by weight of a surfactant package, wherein the surfactant package provides copious foaming to the shaving soap; and about 2 to about 40 parts by weight of mango butter;
    shaving the skin surface; and
    applying an aftershave gel to the skin surface, wherein the aftershave gel further comprises about 0.5% to about 1.5% by volume of a base aftershave gel;
    about 0.5% to about 3% by volume of hamamelis; about 1% to about 30% by volume of a first mixture comprising about 0.5 grams to about 10 grams of *camellia sinensis* and about 8 ounces of distilled water; and about 0.05% to about 1% by volume of DMDM hydantoin.

15. The method of claim 14, wherein the base soap further comprises about 5% to about 30% by weight of distilled water; about 2% to about 50% by weight of palm oil; about 2% to about 30% by weight of coconut oil; about 2% to about 40% by weight of castor oil; and about 4% to about 20% by weight of sodium hydroxide.

16. The method of claim 14, wherein preparing the skin surface further comprises saturating a boar's hair brush with warm water, inserting the boar's hair brush into a cup containing the shaving soap, and mixing until a lather develops.

17. The method of claim 16, further comprising applying the lather to the skin surface with the boar's hair brush using a circular motion.

18. The method of claim 14, wherein applying the aftershave gel to the skin surface further comprises:
    providing a dime-sized amount of the aftershave gel on a first hand;
    rubbing the first hand against a second hand so that the aftershave gel is distributed on the first hand and the second hand; and
    distributing the aftershave gel from the first hand to the skin surface with a single downward motion of the first hand, wherein the single downward motion starts at a cheek bone, moves toward a chin, and finishes at a bottom of a neck, so that the skin surface that has been shaved receives the aftershave gel.

19. The method of claim 18, further comprising distributing the aftershave gel from the second hand to the skin surface with a single downward motion of the second hand, wherein the single downward motion starts at the cheek bone, moves toward the chin, and finishes at the bottom of the neck, so that the skin surface that has been shaved receives the aftershave gel.

20. The method of claim 19, wherein the aftershave gel further comprises about 0.2% to about 1.5% by volume of aloe vera; about 0.2% to about 1.5% by volume of a mixture of glyceryl polymethacrylate, propylene glycol and PVM/MA copolymer; and about 0.1% to about 3% by volume of propylene glycol.

* * * * *